United States Patent
Oonuma et al.

[19]

[11] Patent Number: 5,855,847
[45] Date of Patent: *Jan. 5, 1999

[54] APPARATUS FOR AUTOMATICALLY ANALYZING SAMPLE

[75] Inventors: Mitsuru Oonuma, Tokyo; Atushi Ninomiya, Ome; Atsushi Katayama, Kokubunji; Isamu Takekoshi, Tokyo; Ryuji Tao; Hiroyasu Uchida, both of Hitachinaka, all of Japan

[73] Assignee: Hitachi,Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 529,284

[22] Filed: Sep. 15, 1995

[30] Foreign Application Priority Data

Sep. 21, 1994 [JP] Japan .................................. 6-226237

[51] Int. Cl.$^6$ ................................................. G01N 35/00
[52] U.S. Cl. ................................ 422/64; 422/63; 422/65; 436/43; 436/47
[58] Field of Search ................................ 422/63, 64, 67, 422/104, 65; 436/43, 47, 49, 174, 180, 183

[56] References Cited

U.S. PATENT DOCUMENTS

| | | | |
|---|---|---|---|
| 4,170,625 | 10/1979 | Welch | 422/64 |
| 4,234,540 | 11/1980 | Ginsberg et al. | 422/64 |
| 4,322,216 | 3/1982 | Lillig et al. | 422/65 |
| 4,346,056 | 8/1982 | Sakurada | 422/64 |
| 4,456,037 | 6/1984 | Gocho | 141/1 |
| 4,483,823 | 11/1984 | Umetsu et al. | 422/63 |
| 4,906,433 | 3/1990 | Minekane | 422/64 |
| 4,919,887 | 4/1990 | Wakatake | 422/67 |
| 4,961,906 | 10/1990 | Andersen et al. | 422/102 |
| 5,008,082 | 4/1991 | Shaw | 422/65 |
| 5,104,808 | 4/1992 | Laska et al. | 436/48 |
| 5,147,610 | 9/1992 | Watanabe et al. | 422/64 |
| 5,270,211 | 12/1993 | Kelln et al. | 436/43 |
| 5,271,899 | 12/1993 | Carbonari | 422/67 |
| 5,311,426 | 5/1994 | Donohue et al. | 364/413.09 |
| 5,320,809 | 6/1994 | Dunn et al. | 422/64 |
| 5,425,918 | 6/1995 | Healey et al. | 422/64 |
| 5,482,861 | 1/1996 | Clark et al. | 436/48 |

FOREIGN PATENT DOCUMENTS

| | | |
|---|---|---|
| 0 410 645 A2 | 7/1990 | European Pat. Off. . |
| 0 539168 A2 | 10/1992 | European Pat. Off. . |
| 4210963 A1 | 4/1992 | Germany . |
| 4313399 A1 | 4/1993 | Germany . |
| 63-132169 | 6/1988 | Japan . |
| 3-211463 | 9/1991 | Japan . |
| 6-88828 | 9/1992 | Japan . |
| 92/05448 | 4/1992 | WIPO . |

OTHER PUBLICATIONS

Prospeckt Firma WaKo: WAKO–30R, Augomatisches Analysensystem (this reference provided in German).

*Primary Examiner*—Long V. Le
*Attorney, Agent, or Firm*—Fay, Sharpe, Beall, Fagan, Minnich & McKee

[57] ABSTRACT

An object of the present invention is to provide a small and compact analytical apparatus. An input/output device for directing the analytical apparatus and displaying analytical results and operation conditions is detachably provided on a body of the apparatus. Since the input/output device can be fixed to an upper position of the body, the apparatus saves space and can be placed on a desk. The analytical apparatus includes a sample disk and a reagent disk. The diameter of the reagent disk is greater than that of the sample disk, and both disks are arranged at the front of the apparatus so that the center of the sample disk is nearer the operator side than the center of the reagent disk. Therefore, the whole arrangement is compact, and the apparatus itself is compact.

29 Claims, 6 Drawing Sheets

APPARATUS FOR AUTOMATICALLY ANALYZING SAMPLE

BACKGROUND OF THE INVENTION

1. Field of the Invention

The present invention relates to an analytical apparatus, and particularly to an apparatus for analyzing a sample such as human blood or urine, for example, in the field of clinical biochemistry, or a sample such as blood or urine of domestic animals.

2. Description of the Related Art

A conventional such an analytical apparatus comprises reaction vessels which are doubled or tripled for increasing capacity so that all reactions can simultaneously be effected and for preventing occurrence of contamination of reagents with each other, which are arranged in rows isolated from each other, and which are washed in each reaction process so as to permit continuous treatment, as disclosed in, for example, Japanese Patent Unexamined Publication No. 6-88828.

The above conventional apparatus has the problem that it has not been investigated with respect to a decrease in size of the apparatus for automatically analyzing a sample such as blood or urine of human and domestic animals, and requires a large space. There is also the problem that the arrangement of a keyboard for controlling the apparatus and a display has not been sufficiently investigated, and thus, the apparatus is unsatisfactory in respect to the ease of operation and the prevention of error.

SUMMARY OF THE INVENTION

In order to solve the above problems, in accordance with a first aspect of the present invention, an apparatus for analyzing human blood or urine comprises a body which contains sample holding means, reagent holding means, reaction vessels for reacting samples and reagents, and analytical means for analyzing the reaction solution obtained from reaction in each of the reaction vessels; operation means for controlling reaction and analytical operations; and display means for displaying information about the reaction and analytical operations; wherein the operation means and the display means are formed in one unit as an analytical input/output device which is fixed to the body of the analytical apparatus through detachable fixing means.

In accordance with a second aspect of the present invention, an analytical apparatus comprises sample holding means on which many sample containers can be loaded, reagent holding means on which reagents can be loaded, reaction means for reacting a sample and reagents, pipetting means for pipetting the sample and the reagents in each of reaction vessels, analytical means for analyzing the reaction solution obtained from reaction in each of the reaction vessels, and an input/output device provided with control means for controlling the above means and display means for displaying information about the operations of the means, wherein the sample holding means and the reagent holding means are arranged on the operator side, the pipetting means is disposed at the back of the sample holding means and the reagent holding means, and the input/output device is provided in an upper portion at the back of the sample holding means.

In the analytical apparatus in accordance with the first aspect of the invention, since the input/output device can be mounted on the body or provided at a position separate from the body, the operation position can freely be selected according to circumstances, thereby facilitating the operation of the device. In the analytical apparatus in accordance with the second aspect of the invention, the sample holding means, the reagent holding means and the pipetting means can compactly be arranged, and a sample can be set while operating the input/output device because the input/output device is provided at the back of the sample holding means, thereby making the apparatus compact and easy to operate.

The same effect can be obtained by applying the present invention to an apparatus for automatically analyzing a sample such as blood or urine of animals, for example, cows, horses, pigs, fowls, dogs and cats which include blood circulation through the body.

DESCRIPTION OF THE PREFERRED EMBODIMENTS

Figure 1:
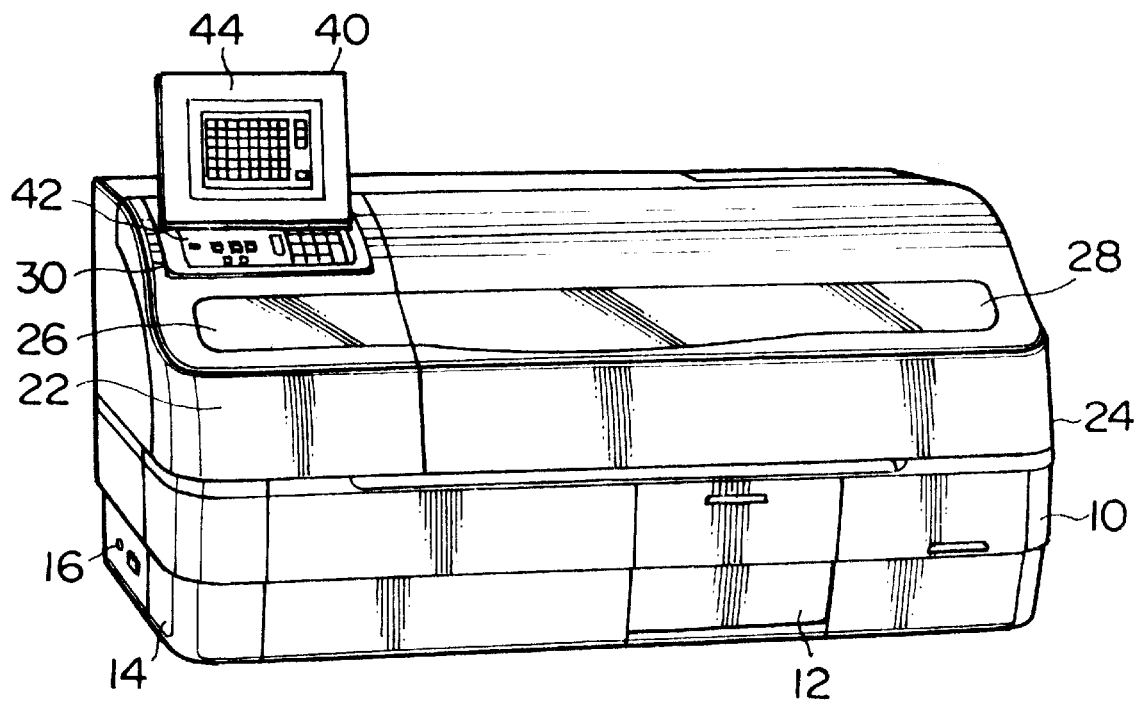
FIG. 1 is a drawing showing the appearance of an apparatus for analyzing human blood or urine in accordance with a first embodiment of the present invention.
Figure 2:
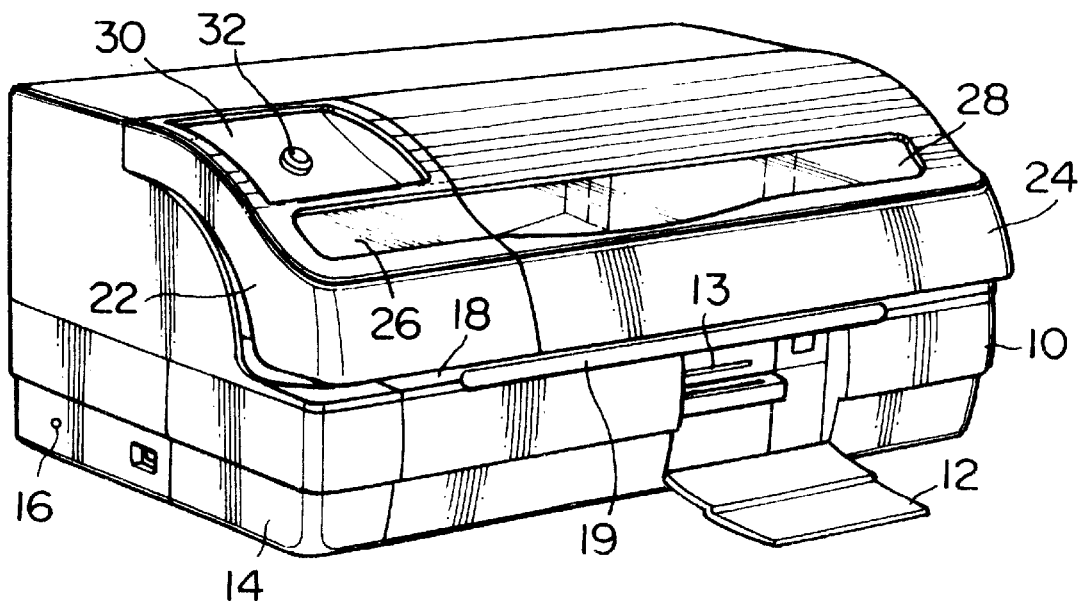
FIG. 2 is a drawing showing the appearance of the analytical apparatus shown in FIG. 1 with an input/output device separated from a body.

An apparatus for analyzing human blood or urine in accordance with an embodiment of the present invention is described below. FIG. 1 is a drawing showing the appearance of an analytical apparatus comprising a body 10 and an input/output device 40, and FIG. 2 is a drawing showing the appearance of the analytical apparatus with the input/output device 40 separated from the body 10 in a state where divided covers 22 and 24 are slightly open. The body 10 comprises the divided first cover 22 and second cover 24, which can be opened and closed independently of each other. Thus, a sample can be set and removed by opening and closing only the cover 22, as described below. Therefore, during opening and closing the cover 22, the reagent holding means and the nozzle of an pipetting device are not damaged by contact therewith and the hand of the operator is not injured.

The first and second covers 22 and 24 are provided with windows 26 and 28, respectively, both of which form a continuous window when the covers 22 and 24 are closed. The windows 26 and 28 are made of the same material such as plastics, glass and the like. Since the windows 26 and 28 are provided, the normal operation of the test apparatus can visually be confirmed even if the covers 22 and 24 are closed. The first cover 22 is provided with an opening 30, i.e., a hole, in which the input/output device 40 having operation means 42 and display means 44 is provided. The opening 30 of the first cover may be either an opening or a notch. As shown in FIG. 2, fixing means 32 for fixing the input/output device 40 is provided at a mounting position of the input/output device 40, a base 41 (refer to FIG. 8) of the input/output device 40 being fitted to the fixing means 32. The display means 44 of the input/output device 40 has a function of a touch panel. However, even if the touch panel is pushed based on the function, the fixing means prevents the input/output device 40 from falling down. A connector 16 for connecting a signal line of the input/output device 40 is provided on a side of the body 10 so as to be used for connecting the signal line when the input/output device 40 is separated from the body 10 and used.

A cover 12 is provided on the body 10 so as to cover a storage device 13 provided for setting a storage medium such as a floppy disk or the like. Since the storage device 13 is retracted from the front side of a table 18 of the body 10, neither sample nor reagent enters the storage device 13 even if it is spilt.

A sample-side corner 14 of the body 10 is removable. Although, in this embodiment, the corner 14 can be removed, the entire side including the corner 14 may be made removable. When this corner 14 is removed, a sample disk, which will be described below, can be removed so that another sample transfer line can be used. This is required when the analytical apparatus is used in a large hospital and a institution building for analyzing large amounts of samples, which are directly provided with sample transfer lines. The analytical apparatus of this embodiment without the sample-side corner 14 is set in a sample conveyance line, and a sample is pipetted by a pipetting device which will be described below, and then analyzed.

Figure 3:
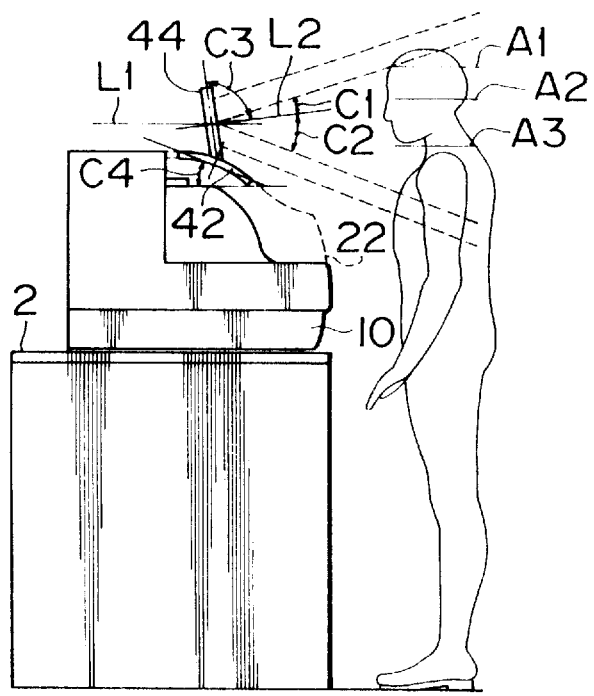
FIG. 3 is a drawing showing a relation between an operator and the analytical apparatus shown in FIG. 1 during operation.
Figure 4:
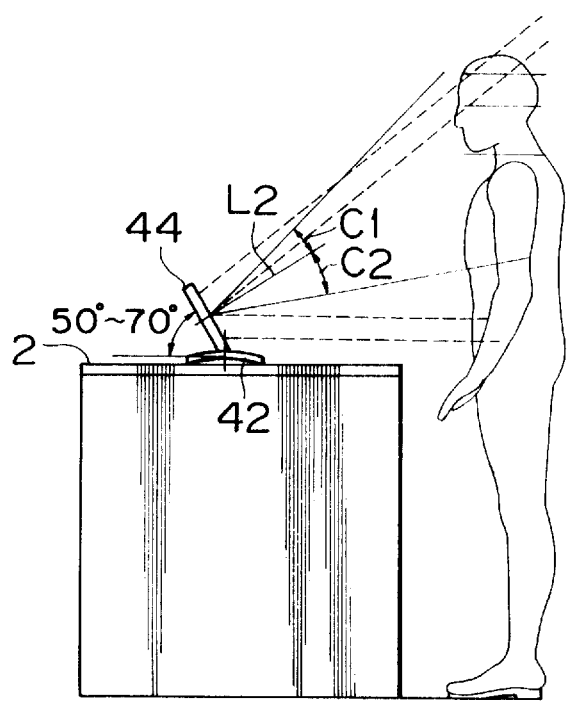
FIG. 4 is a drawing showing a relation between an operator and an input output device separated from the body of the apparatus.

FIGS. 3 and 4 are drawings showing examples of operation conditions of the analytical apparatus of the present invention. FIG. 3 shows an example where the input/output device 40 is used in the state shown in FIG. 1 in which it is mounted on the analytical apparatus, and FIG. 4 shows an example where the input/output device 40 is used in the state shown in FIG. 2 in which it is removed from the apparatus body. FIG. 4 shows only the input/output device 40, with the body 10 omitted. The analytical apparatus of this embodiment is frequently used on a desk 2. The desk 2 has the standard height, for example, a height of 850 mm in Japan, and a height of 900 mm in foreign countries. Liquid crystal display means is used for the display unit 44 shown in FIG. 3, and is preferably set at the height of the eyes of an operator. The average height of the eyes of Japanese women is 1455 to 1600 mm, the average height of the eyes of Japanese men is 1720 to 1740 mm, and the average height of the eyes of European and American foreign men is 1820 to 1850 mm. Thus, the height of the liquid crystal display means provided on the body of the analytical apparatus is preferably set to 1490 mm to 1765 mm.

The inclination C3 of the liquid crystal display plane with respect to horizontal line L1 is preferably 100° to 130°. If the display plane is perpendicularly set, i.e., set at 90°, the display plane might be damaged with nails when it is touched with the hand. Particularly, when the display plane has the touch panel function, a nail scratch is an important problem. In FIG. 3, angles C1 and C2 show an angle range where the liquid crystal display plane can be seen well, and angle C1 which is an upward angle with respect to perpendicular line L2 is 10°. With an upward angle C1 of not more than 10°, the liquid crystal display plane can be seen well, and, with an upward angle C1 of not less than this angle, the display plane cannot be seen well. Angle C2 which is a downward angle with respect to perpendicular line L2 is 30°. With a downward angle of not less than 30°, the display plane cannot be seen well. Since angle C2 is greater than angle C1, when the display plane is at an angle greater than 90°, i.e, right angle to the horizontal line L1, the display plane can comply with persons having various heights. In consideration of these points, the angle C3 with respect to line L1 is preferably 100° to 300°.

In FIG. 3, the input/output device 40 is fixed to the body 10 of the analytical apparatus so that operation means 42 thereof is downwardly inclined nearer to the operator side. This downward inclination in the direction nearer to the operator side facilitates the operation of the keyboard of the operation means 42, and decreases the fatigue of the operation. The operation means 42 also becomes easy to see. The angle C4 between the operation means 42 and line L1 is preferably 5° to 30°. Within this angle range, the angle of the hand placed on the keyboard is suitable for the angle of the wrist, thereby enabling smooth operation. FIG. 4 shows an example where the input/output device shown in FIG. 3 is removed from the body 10 and placed on the desk 2. Since the input/output device 40 is placed directly on the desk 2, not on the body 10, the angle of the liquid crystal display plane with respect to the horizontal line must be larger than that shown in FIG. 3. Thus, the position of the eye is within the range of angles Cl and C2 shown in FIG. 3. Therefore, in both operation states shown in FIGS. 3 and 4, the liquid crystal display plane can be seen well.

As shown in FIGS. 1 to 3, each of the covers 22 and 24 comprises the combination of curved surfaces including an outwardly curved surface and an inwardly curved surface. The inwardly curved surface is formed on the operator side, and the outwardly curved surface is at the rear side. The operation means of the input/output device 40 is disposed in the outwardly curved surface, and the windows 26 and 28 are disposed in the inwardly curved portion so that the angle of the downward inclination of the operation means 42 can be increased, and the operating characteristics can thus be improved. Since the window portion is formed in the inwardly curved surface portion on the operator side of the input/output device 40, the inside of the apparatus can easily be seen through the windows.

Figure 5:
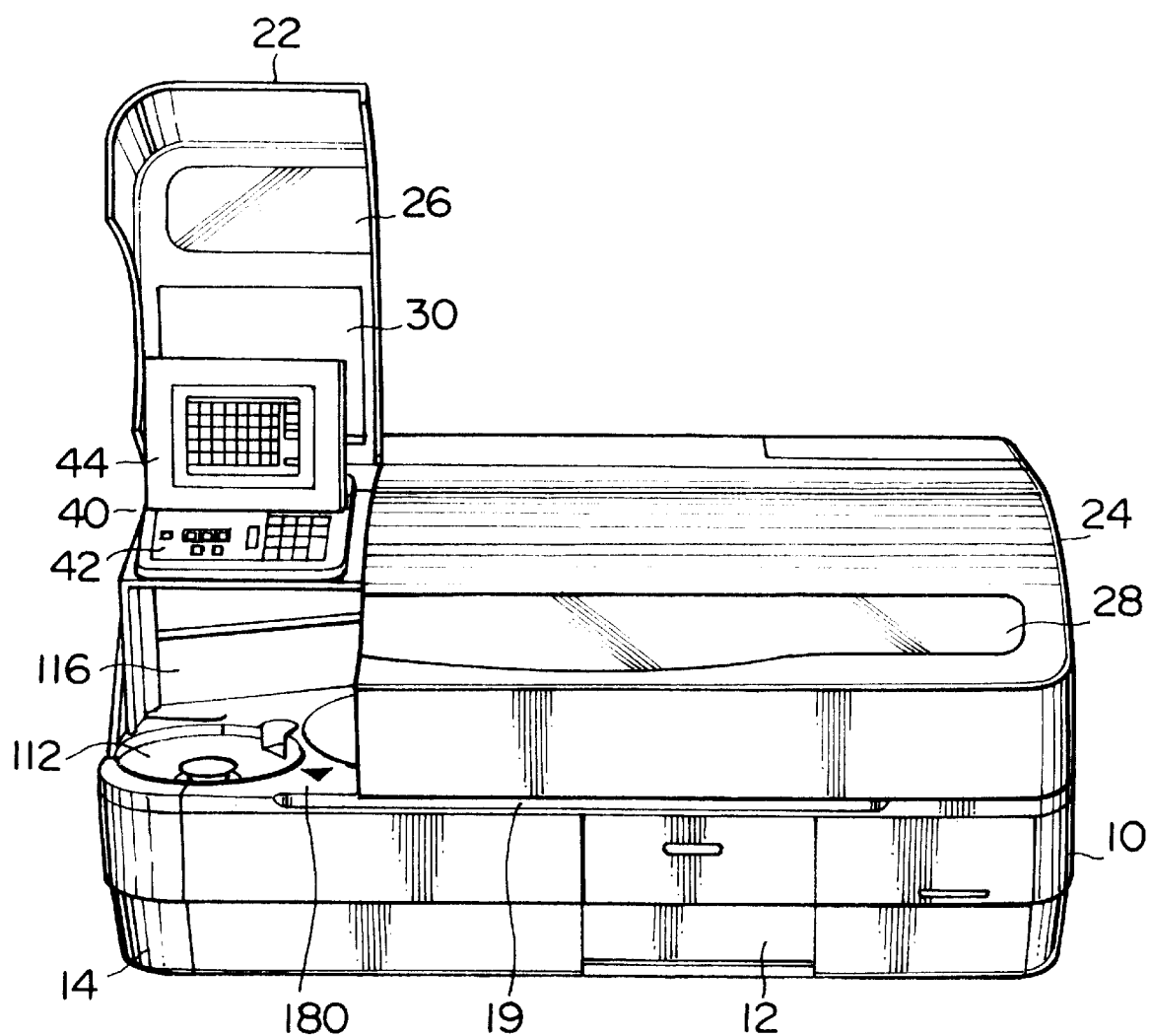
FIG. 5 is a drawing showing the analytical apparatus of the present invention in a state where one of divided covers is open.
Figure 6:
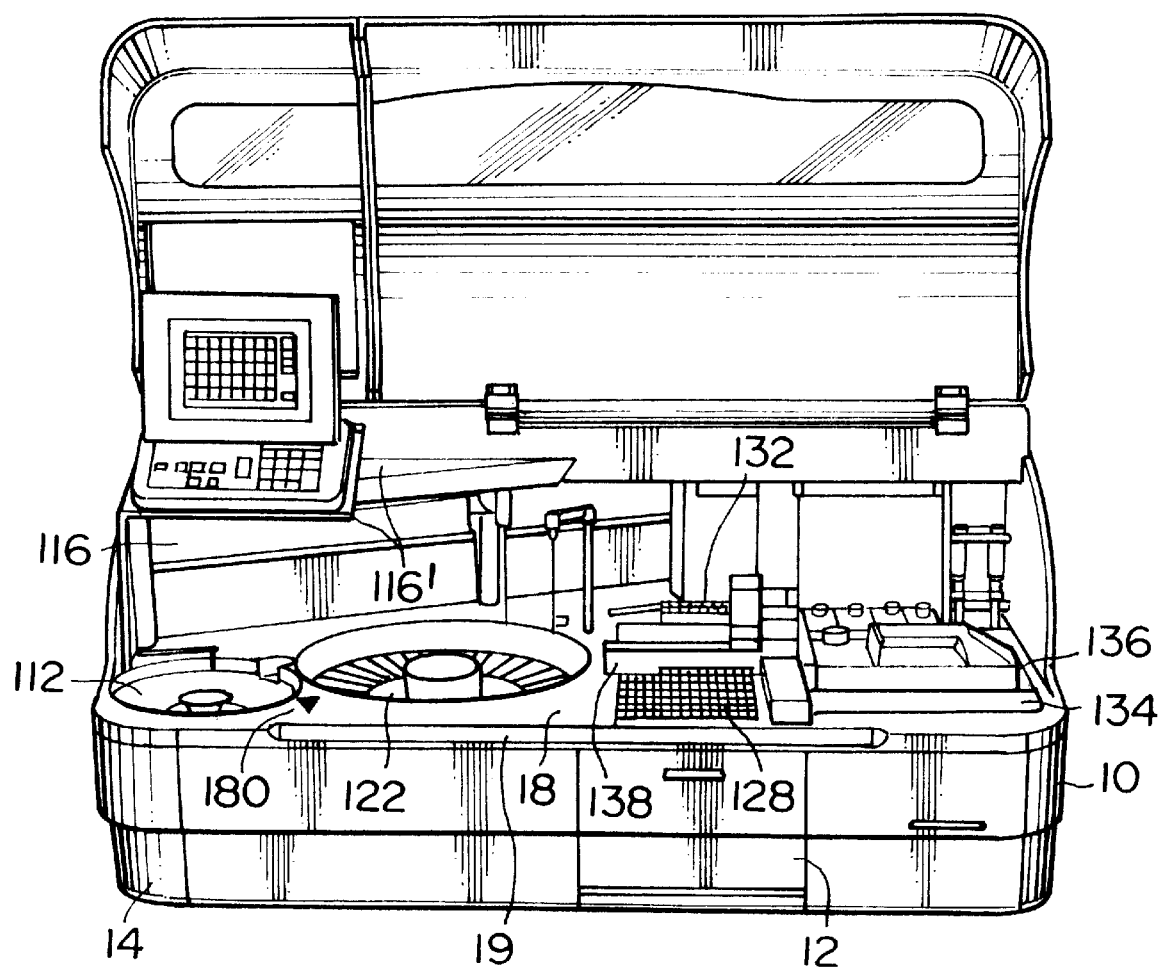
FIG. 6 is a drawing showing the analytical apparatus of the present invention in a state where both divided covers are open.
Figure 7:
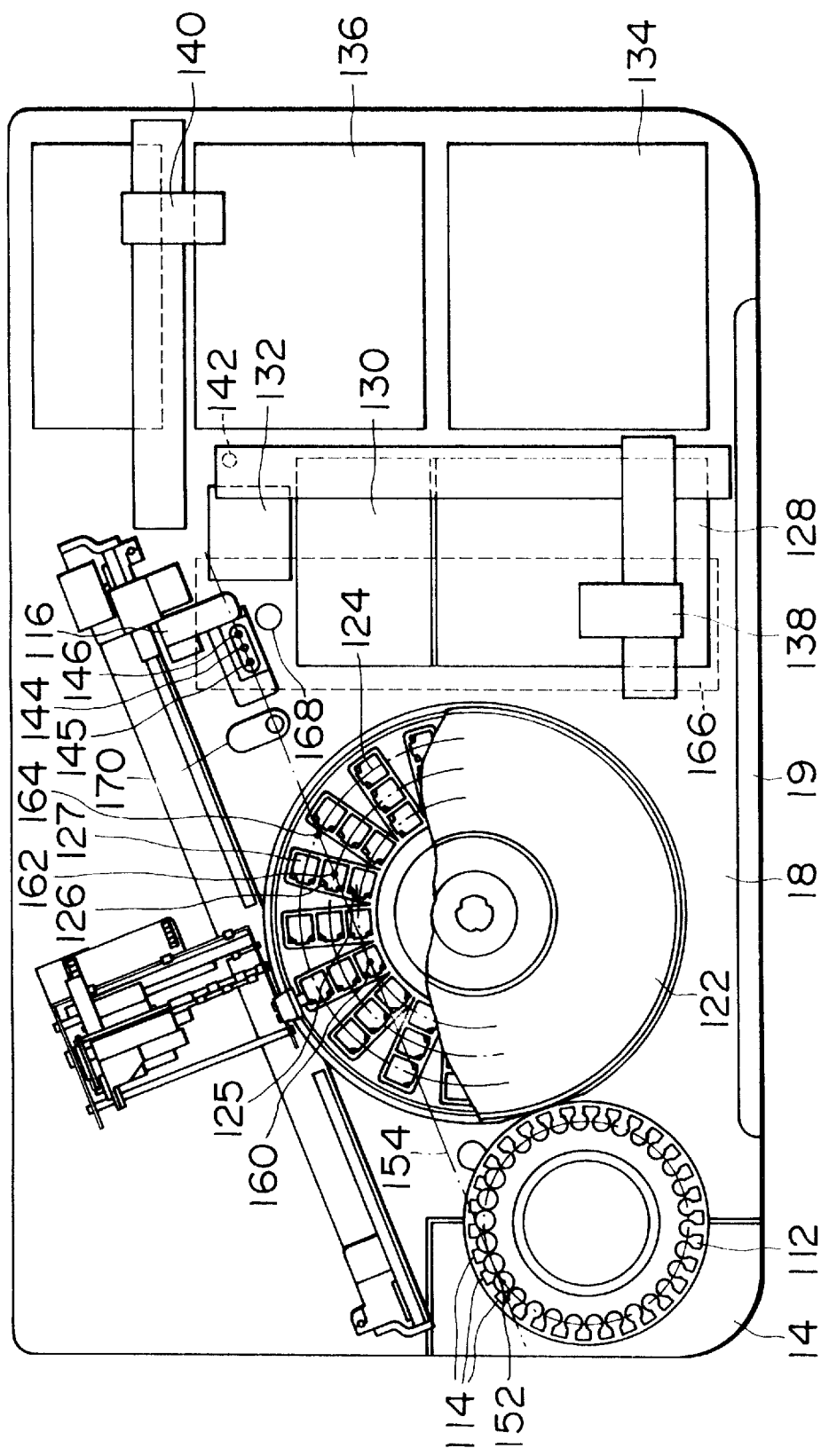
FIG. 7 is a drawing showing an arrangement of elements in the body of the analytical apparatus.

FIG. 5 shows a state where only the first cover 22 is open, FIG. 6 shows a state where both the first and second covers 22 and 24 are open, and FIG. 7 shows the arrangement of a sample disk 112, a reagent disk 122, a pipetting device 116, etc. on the surface of a table 18. In the table 18 are formed two circular holes in one of which the sample disk 112 is disposed, the reagent disk 122 being disposed in the other hole. Many sample vessels 114 each of which contains a sample such as serum, urine or the like are circumferentially loaded on the sample disk 112. On the other hand, many reagent bottles 124 containing reagents are concentrically loaded on the reagent disk 122 and are maintained at low temperature below the predetermined temperature for preventing chemical changes of the reagents. In this embodiment, packages each comprising three bottles 124 in the radial direction of the disk 122, which respectively contains three reagents 125, 126 and 127, are formed. Many disposable nozzle tips which are made of, for example, polypropylene, and which are relatively inexpensive are held in a tip rack 128. Many vessels in each of which reaction is effected are held in a vessel rack 130. A reaction unit (incubator) 132 for keeping a constant temperature and effecting reaction at this constant temperature is provided at the back of the vessel rack 130. A gripper mechanism 138 is adapted for taking a nozzle tip out of the tip rack 128 for holding many nozzle tips and transferring the tip to a tip buffer 144, and further taking a vessel out of the vessel rack 130 for holding many vessels and transferring a vessel to a vessel buffer 145 which is a place for temporarily retracting the vessel.

The pipetting device 116 has the function to pipet samples and reagents, and is disposed at the back of the sample disk 112 and the reagent disk 122, as shown in FIG. 7. The pipetting device 116 is linearly moved in the horizontal direction from a sample suction position 152 to a nozzle disposal position 146. The intersections between the horizontal movement locus 154 of the pipetting device 116 and the loci of circumferential movements of the reagent bottles 125, 126 and 127 respectively correspond to suction positions 160, 162 and 164 of the reagents. An analytical unit 140 sucks a reaction solution at a reaction solution suction position 142 and analyzes the reaction solution. Reference numeral 166 denotes a disposal box in which the used nozzle tip and the used vessel are disposed of from a nozzle tip disposal position 146 and a vessel disposal position 168, respectively. Reference numeral 170 denotes a mechanism for washing the nozzle tips, and reference numeral 134 denotes a device for controlling the entire apparatus.

As shown in FIG. 7, the diameter of the reagent disk 122 is greater than that of the sample disk 112, and both disks are arranged so that the two disks are as near the operator side as possible, and the center of the sample disk 112 is nearer the operator side than the center of the reagent disk 122. As a result, the pipetting device 116 is obliquely arranged at the back of both disks. This arrangement can make the entire apparatus compact and decrease the area required for the apparatus. On the table 18 is provided a mark 180 (refer to FIGS. 5 and 6) which indicates a reference sample position of the sample disk. This mark 180 is used as a reference position where samples are successively set in the sample disk 112. The control device 134 senses the rotational angle of a sample and stops the rotation of the sample disk 112 so that the reference holding position corresponds to the mark 180 and stops at the position.

When a sample which is required to be rapidly analyzed, i.e., tested, is transferred to the apparatus during a test, the control device 134 displays the set position of the sample on the input/output device 40 and controls the stop position of the sample disk 112 so that the set position corresponds to the mark 180. Therefore, the sample may be set at the position indicated by the mark 180, thereby preventing the occurrence of error.

The front side of the table 18 is cut, as shown by reference numeral 19. Since the front edge of the table 18 is not extruded, but cut, stains of the reagents and sample can easily be wiped off. The corner 14 is removable, and the sample holding means is removed at the same time when the corner 14 is removed. Therefore, when a sample transfer line is provided in a hospital or the like, the transfer line can be used in place of the sample holding means.

FIG. 6 shows the state where a cover is attached to the table 18 shown in FIG. 7. A protective plate 116' serving as a protective cover is provided above the pipetting device 116 so as to protect the sliding mechanism of the pipetting device 116, the input/output device being detachably attached to the protective plate 116'. FIG. 5 shows the state where only the cover 22 is open. Since the cover 22 is provided so as to cover the sample disk 112, the sample can be put in and out of the sample disk 112 by opening only the cover 22. In the state shown in FIG. 5, since the cover 24 covers most of the reagent disk 122 or at least the reagent suction pipetting point of the reagent disk 122, the reagent disk 122 is protected against dust or the like at the exchange of the sample disk. In addition, the cover 24 prevents the apparatus from being damaged and the hand from being injured by contact with the reagent disk 122. The sample set position displayed on the display unit 44 with the cover 22 closed can be seen in the state where the sample is set with the cover 22 open, as shown in FIG. 5. Thus, the sample set position can easily be confirmed while seeing the display unit 44. As shown in FIG. 5, the width of the input/output device 40 is smaller than the width of the cover 22.

Figure 8:
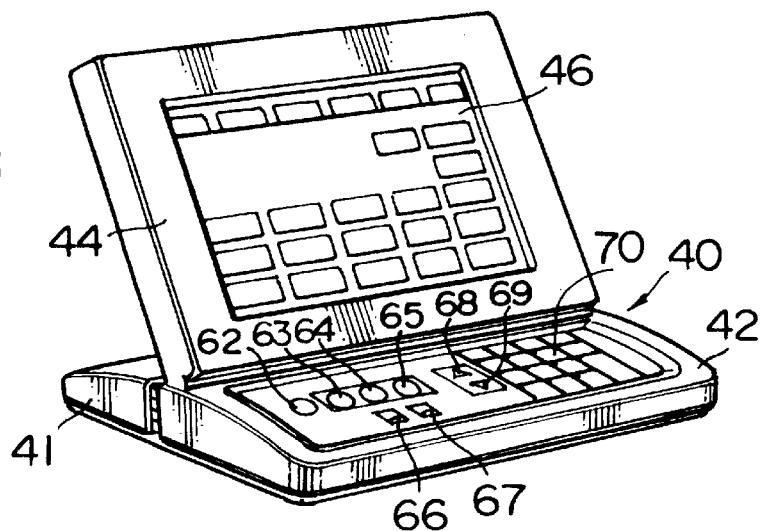
FIG. 8 is a perspective view showing the input/output device.
Figure 9:
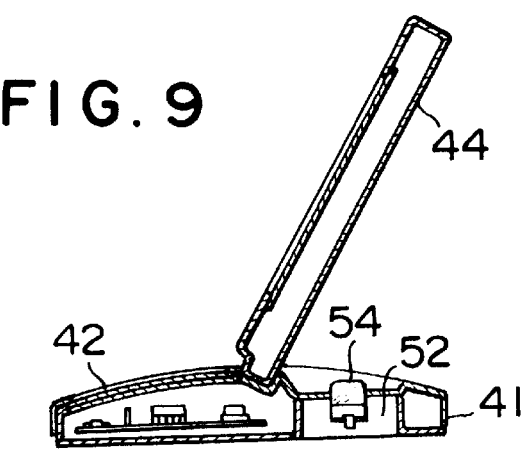
FIG. 9 is a sectional view showing the input/output device shown in FIG. 8.
Figure 10:
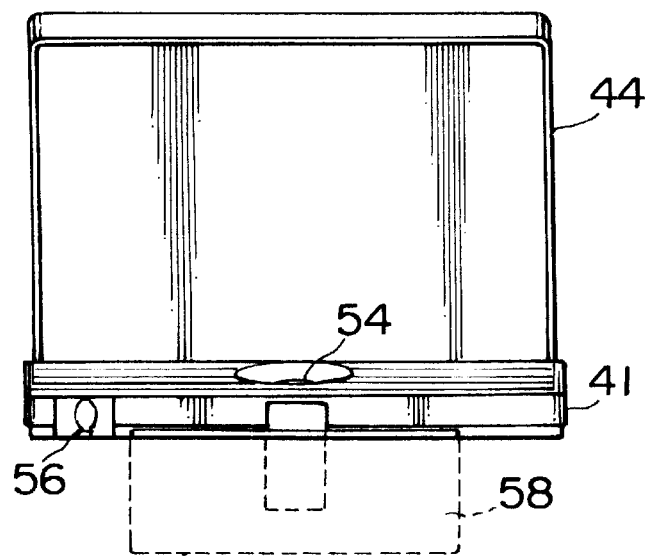
FIG. 10 is a rear view showing the input/output device shown in FIG. 8.

FIGS. 8, 9 and 10 show the input/output device 40. FIG. 8 is a perspective view showing the front side of the input/output device 40, FIG. 9 is a sectional view thereof, and FIG. 10 is a rear view thereof. The input/output device 40 comprises the base 41, and the operation means 42 and the display means 44 both of which are mounted on the base 41. The start key 63 shown in FIG. 8 is pushed in a state where preparation for an analytical operation is completed, i.e., after test items of each of samples are selected and specified by a touch panel 46. When a pipetting operation is started by the key 63, reaction is started, and the reaction solution is analyzed. A stop key 65 is adapted for stopping pipetting and analyzing operations. A sampling stop key 64 is provided between the start key 63 and the stop key 65. The keys 63 and 65 are used for operations which are contrary to each other, and thus a mistake in pushing the keys causes a significant effect. This trouble is avoided by providing another key between both keys. The sampling stop key 64 stops the pipetting operation, but analysis of the reaction solution is continued. Additional samples can be set by pushing the sampling stop key 64.

A key 62 is used when a sample is desired to be rapidly tested, and has the same function as the stop key 65. However, the key 62 further has the function to permit a test with a higher degree of preference. Namely, when the pipetting operation is stopped by pushing the key 62, and a sample is then set, this sample is treated in preference to other samples. In other words, the sample is pipetted and tested before tests of the other samples. Keys 68 and 69 are screen operating keys which must be disposed on the operation means, not on the touch panel of the display means 44. A ten-key pad 70 is preferably provided on the operation means because difficulties arise in operating the ten key pad 70 on the touch panel.

FIG. 9 is a sectional view of the input/output device 40. Mechanisms 52 and 54 which form a loading and unloading device are provided on the base 41 so that the mechanism 52 comprising a recessed portion engages the fixing means 32 provided on the body. When the mechanism 54 comprising a button is strongly pushed, the engagement between the recessed portion 52 and the fixing means 32 is released. Another method considered as a detachable fixing method can also be used.

FIG. 10 is a rear view of the input/output device 40. On the base 41 are provided a power supply, a connector 56 for a signal line for transmitting and receiving signals to and from the control device of the body, and the above-described push button 54 as a detachable mechanism. Extension means 58 is provided on the base 41 so that, if required, it can be drawn out of the base 41 for preventing the input/output device 40 from falling down even if the touch panel 46 shown in FIG. 8 is pushed. Although a structure in which the extension means 58 can be inserted into the base 41, and drawn out of the base 41 if required is simplest, the extension means may be formed as a separate unit and attached to the base 41 if required.

As described above, in this embodiment, the input/output device 40 may be used in either the state where it is mounted on the upper portion of the body 10 or the state where it is removed therefrom. The input/output device 40 is used for selecting test contents of a sample, starting and stopping a test, confirming test conditions and results by display, adding and changing a test sample, etc. However, unlike keyboards of a personal computer and word processor, the input/output device 40 is not constantly used, a sample is automatically tested after directions, and test conditions may be confirmed at intervals. Unlike ordinary OA apparatus, the input/output device 40 is used by an operator in a standing posture in a place of work where samples and reagents are handled. The input/output device 40 has the advantage that the area for use of the device can be decreased, and the device itself can be made compact. The device also has the advantage that since it is used by an operator in a standing posture, the device can be fixed to the body of the apparatus. The analytical apparatus of the present invention is made compact, and thus has the advantage that it can be used on a desk, and save space, as compared with an apparatus which must be placed on a floor.

What is claimed is:

1. An analyzing apparatus for detecting a reaction result, the apparatus comprising:
    a sample holding device for holding a sample vessel;
    a reagent holding device for holding a reagent vessel, said reagent holding device being rotatable about an axis that is nonconcentric with said sample holding device;
    a pipetting device for pipetting a predetermined volume of sample in said sample vessel and a predetermined volume of reagent in said reagent vessel into said reaction vessel, wherein said pipetting device moves linearly in a horizontal movement locus, and wherein said pipetting device is so arranged to be positioned over said sample holding device, said reagent holding device and said reaction vessel at a location offset from a center of said reagent holding device remote from a front edge of the apparatus.

2. The analyzing apparatus according to claim 1 further including a protective plate disposed above said pipetting device.

3. An analyzing apparatus for detecting a reaction result according to claim 1, further comprising:
    analytical means for analyzing the reaction solution obtained by reaction in said reaction vessel;
    a body containing said sample holding device, reagent holding device, reaction vessel, pipetting device and analytical means; and
    indication means for indicating a reference position of said sample holding device.

4. An analyzing apparatus according to claim 3, wherein said sample holding device has a circular form and is placed in a substantially circular hole which is formed in a table of said body, and a mark as means for indicating said reference position is provided on said table.

5. An analyzing apparatus according to claim 4, further comprising a control device for controlling an analytical operation, and an input device for directing control by said control device, wherein said control device controls said sample holding device based on a direction by said input device so that a loading position of a test sample on said sample holding device corresponds to the position of said mark.

6. An analyzing apparatus for detecting a reaction result, the apparatus comprising;
    a sample holding device for holding a sample vessel;
    a reagent holding device for holding a reagent vessel;
    a reaction vessel for causing a sample and a reagent to react with each other;
    a pipetting device for pipetting a predetermined volume of sample in said sample vessel and a predetermined volume of reagent in said reagent vessel into said reaction vessel, characterized in that:
    said reagent holding device is rotatable and is circular in shape;
    said sample holding device is rotatable and is circular in shape, and is nonconcentric with said reagent holding device; and
    said pipetting device moves linearly in a horizontal movement locus, wherein said pipetting device is so arranged as to be positioned above said sample holding device, said reagent holding device and said reaction vessel and at a location offset from a center of said reagent holding device and a center of said sample holding device remote from a front edge of the apparatus.

7. The analyzing apparatus according to claim 6 wherein:
    said reagent holding device has a diameter thereof which is formed larger than a diameter of said sample holding device and, further, said sample holding device has a center thereof which is positioned closer to the front edge than a center of said reagent holding device; and
    said horizontal movement locus of said pipetting device is positioned obliquely relative to said reagent holding device and said sample holding device.

8. The analyzing apparatus according to claim 6 further including a protective plate disposed above said pipetting device.

9. The analyzing apparatus according to claim 6, further comprising:
    an input/output device detachably disposed behind the sample holding device; and
    a cover for the sample holding device;
    wherein the input/output device can be operated whether the cover is open or closed; and
    wherein a sample can be set into the sample holding device when the cover is open.

10. The analyzing apparatus according to claim 6, wherein said sample holding device is disposed on a first side of said reagent holding device, and said reaction vessel is disposed on a second side of said reagent holding device.

11. The analyzing apparatus according to claim 6, wherein said pipetting device is obliquely arranged behind the sample holding device and the reagent holding device.

12. The analyzing apparatus according to claim 6, further comprising a cover having first and second independently operable cover portions, wherein the first cover portion covers the sample holding device and the second cover portion covers the reagent holding device and the reaction vessel.

13. An analyzing apparatus for detecting a reaction result, the apparatus comprising:
    a body having a cover;
    a sample holding device provided on said body, for holding a sample vessel;

a reagent holding device provided on said body for holding a reagent vessel;

a reaction vessel provided on said body, for causing a sample and a reagent to react with each other; and a pipetting device for pipetting a predetermined volume of sample in said sample vessel and a predetermined volume of reagent in said reagent vessel into said reaction vessel, characterized in that:

said reagent holding device is rotatable and is circular in shape;

said sample holding device is disposed on a first side of said reagent holding device;

said reaction vessel is disposed on a second side of said reagent holding device; and said pipetting device is so arranged as to be linearly moveable in a horizontal movement locus from said sample holding device to said reaction vessel over said reagent holding device.

14. The analyzing apparatus according to claim 13, further including a protective plate disposed above said pipetting device.

15. The analyzing apparatus according to claim 13 wherein said cover has first and second independently operable cover portions, said first cover portion covering said sample holding device and said second cover portion covering said reagent holding device.

16. An analyzing apparatus for detecting a reaction result, the apparatus comprising:

a body having a cover;

a sample holding device provided on said body, for holding a sample vessel;

a reagent holding device provided on said body, for holding a reagent vessel;

a reaction vessel provided on said body, for causing a sample and a reagent to react with each other; and a pipetting device for pipetting a predetermined volume of sample in said sample vessel and a predetermined volume of reagent in said reagent vessel into said reaction vessel, characterized in that:

said reagent holding device is rotatable and is circular in shape;

said sample holding device is disposed on a first side of said reagent holding device;

said reaction vessel is disposed on a second side of said reagent holding device; and a horizontal movement locus of said pipetting device is continuous from said sample holding device to said reaction vessel and, further, said pipetting device is so arranged as to be moved from said sample holding device through said reagent holding device to said reaction vessel and at a location offset from a center of said reagent holding device remote from a front edge of said body.

17. The analyzing apparatus according to claim 16 further including a protective plate disposed above said pipetting device.

18. The analyzing apparatus according to claim 16 wherein said cover has first and second independently operable cover portions, said first cover portion covering said sample holding device and said second cover portion covering said reagent holding device.

19. The analyzing apparatus according to claim 16, further comprising:

an input/output device detachably disposed behind the sample holding device; and a cover for the sample holding device;

wherein the input/output device can be operated whether the cover is open or closed; and wherein a sample can be set into the sample holding device when the cover is open.

20. The analyzing apparatus according to claim 16, wherein said pipetting device is obliquely arranged behind the sample holding device and the reagent holding device.

21. The analyzing apparatus according to claim 16, wherein said cover has first and second independently operable cover portions, the first cover portion covering the sample holding device and the second cover portion covering the reagent holding device and the reaction vessel.

22. An analyzing apparatus comprising:

a body which has a sample holding device, a reagent holding device, a reaction vessel, and a pipetting device, wherein said reagent holding device is formed by a rotatable circular disk, said sample holding device is disposed on a first side of said reagent holding device, and said reaction vessel is disposed on a second side of said reagent holding device, wherein said pipetting device is disposed in back of said sample holding device and said reagent holding device;

a cover for covering said sample holding device, said reagent holding device, and said pipetting device, wherein said pipetting device is arranged to move linearly across said sample holding device, said reagent holding device, and said reaction vessel, and said pipetting device moves in a horizontal movement locus that is continuous from said sample holding device to said reaction vessel;

a protective plate disposed above said pipetting device and below said cover;

an input/output device for controlling said analyzing apparatus; and a display device.

23. The analyzing apparatus according to claim 22, wherein said sample holding device has a rotatable disk smaller than said reagent holding device, and said rotatable disk of said sample holding device has a center thereof which is located closer to a front edge of said body than a center of rotation of said reagent holding device; and said pipetting device is obliquely disposed such that the center of rotation of said sample holding device is positioned proximate said front edge relative to said horizontal movement locus.

24. An analyzing apparatus comprising:

a body which is provided with a sample holding device, a reagent holding device, a reaction vessel and a pipetting device, wherein said reagent holding device is formed by a rotatable circular disk, said sample holding device is disposed on a first side of said reagent holding device, and said reaction vessel is disposed on a second side of said reagent holding device, said pipetting device being disposed rearward of said sample holding device and said reagent holding device and moving linearly in a horizontal movement locus that is continuous from said sample holding device to said reaction vessel;

a cover for covering said sample holding device, said reagent holding device and said pipetting device;

a protective cover above said pipetting device and below said cover;

an input/output device for controlling said analyzing apparatus; and a display device, said input/output device and said display device being disposed on said protective cover.

25. The analyzing apparatus according to claim 24 wherein a notch is provided in said cover, and said input/output device and said display device project through said notch when said cover is closed.

26. The analyzing apparatus according to claim 24 wherein a notch is provided in said cover, and said input/output device and said display device are detachably mounted to said body through said notch in said cover.

27. An analyzing apparatus comprising a body which is provided with a sample holding device, a reagent holding device, a reaction vessel and a pipetting device, wherein said reagent holding device is formed by a rotatable circular disk, said sample holding device is disposed on a first side of said reagent holding device, and said reaction vessel is disposed on a second side of said reagent holding device, said pipetting device being disposed rearward of said sample holding device and said reagent holding device and moving linearly in a horizontal movement locus that is continuous from said sample holding device to said reaction vessel;

a cover for covering said sample holding device, said reagent holding device and said pipetting device;

an input/output device for controlling said analyzing apparatus; and a display device, characterized in that:

said reagent holding device is formed by a rotatable circular disk, said sample holding device is disposed on one side of said reagent holding device, and said reaction vessel is disposed on the other said of said reagent holding device; and an opening is provided in said cover, and said display device is mounted to said body such that said input/output device and said display device project through said opening when said cover is closed.

28. An analyzing apparatus comprising:

a body which is provided with a sample holding device, a reagent holding device, a reaction vessel and a pipetting device, wherein said reagent holding device is formed by a rotatable circular disk, said sample holding device is disposed on a first side of said reagent holding device, and said reaction vessel is disposed on a second side of said reagent holding device, said pipetting device being disposed rearward of said sample holding device and said reagent holding device and moving linearly in a horizontal movement locus that is continuous from said sample holding device to said reaction vessel;

a cover for covering said sample holding device, said reagent holding device, and said pipetting device;

wherein said cover has a first cover for covering said sample holding device and a second cover for covering said reagent holding device;

an input/output device for controlling said analyzing apparatus; and a display device.

29. The analyzing apparatus according to claim 28, wherein a notch is provided in said first cover, and said display device is mounted to said body such that said input/output device and said display device project through said notch when said first cover is closed.

* * * * *